(12) United States Patent
McMinn

(10) Patent No.: US 11,583,297 B2
(45) Date of Patent: Feb. 21, 2023

(54) MULTIFUNCTIONAL SPACER FOR KNEE SURGERY TO ACHIEVE BALANCED RESECTION

(71) Applicant: Derek James Wallace McMinn, West Midlands (GB)

(72) Inventor: Derek James Wallace McMinn, West Midlands (GB)

( * ) Notice: Subject to any disclaimer, the term of this patent is extended or adjusted under 35 U.S.C. 154(b) by 523 days.

(21) Appl. No.: 16/442,950

(22) Filed: Jun. 17, 2019

(65) Prior Publication Data
US 2019/0380721 A1    Dec. 19, 2019

(30) Foreign Application Priority Data

Jun. 18, 2018 (GB) ...................................... 1809938

(51) Int. Cl.
| | | |
|---|---|---|
| *A61B 17/64* | (2006.01) | |
| *A61F 2/46* | (2006.01) | |
| *A61B 17/17* | (2006.01) | |
| *A61F 2/38* | (2006.01) | |
| *A61B 17/02* | (2006.01) | |
| *A61F 2/30* | (2006.01) | |

(52) U.S. Cl.
CPC .......... *A61B 17/1764* (2013.01); *A61F 2/389* (2013.01); *A61F 2/461* (2013.01); *A61F 2/4684* (2013.01); *A61B 2017/0268* (2013.01); *A61F 2002/30616* (2013.01); *A61F 2002/4615* (2013.01); *A61F 2002/4658* (2013.01)

(58) Field of Classification Search
CPC .................... A61F 2/461; A61F 2/4684; A61F 2002/4658; A61B 17/1764; A61B 2017/0268
See application file for complete search history.

(56) References Cited

U.S. PATENT DOCUMENTS

| | | | | |
|---|---|---|---|---|
| 8,167,888 | B2 * | 5/2012 | Steffensmeier | ...... A61B 17/155 606/88 |
| 10,271,965 | B2 * | 4/2019 | Dungy | .................. A61F 2/4657 |
| 2006/0089653 | A1 | 4/2006 | Auger et al. | |
| 2006/0241639 | A1 | 10/2006 | Kuczynski et al. | |
| 2010/0305711 | A1 * | 12/2010 | McKinnon | ............ A61F 2/4684 623/20.32 |
| 2015/0209053 | A1 | 7/2015 | Wilkinson et al. | |
| 2017/0333058 | A1 | 11/2017 | Cabot | |

FOREIGN PATENT DOCUMENTS

WO    2012004580 A1    1/2012

OTHER PUBLICATIONS

Combined Search and Examination Report relating to the priority application GB 1809938.2, dated Nov. 27, 2018, 3 pages.
Combined Search and Examination Report issued for the corresponding UK patent application GB 1908711.3, dated Dec. 10, 2019, 7 pages.

* cited by examiner

*Primary Examiner* — Nicholas W Woodall
(74) *Attorney, Agent, or Firm* — Morgan, Lewis & Bockius LLP

(57) ABSTRACT

A multifunctional spacer for knee surgery is described comprising a main body configured for use with a single femoral condyle and having an anterior portion of a first height and a posterior portion of a second height, wherein the second height is greater than, equal to or less than the first height. In addition, the anterior portion and/or the posterior portion is provided with an attachment mechanism for selective attachment of a height adjuster.

12 Claims, 13 Drawing Sheets

MULTIFUNCTIONAL SPACER FOR KNEE SURGERY TO ACHIEVE BALANCED RESECTION

RELATED APPLICATION

This application claims the benefit of and priority to United Kingdom Application No. 1809938.2, filed Jun. 18, 2018. The entire disclosure of this application is hereby incorporated by reference.

FIELD OF THE INVENTION

The present invention relates to a multifunctional spacer for knee surgery to achieve balanced resection. Particularly, but not exclusively, the invention relates to a multifunctional spacer for use in total knee replacement (TKR) operations.

BACKGROUND

The Applicant's earlier patent, GB2445620B, describes instrumentation for use in knee surgery, upon which the present invention builds. The content of GB2445620B is therefore incorporated by reference into the present disclosure.

Prosthetic knee replacement surgery is employed to replace damaged or diseased parts of the knee. A particularly common disease that affects joints such as the knee is osteoarthritis. This disease usually increases in severity with age and leads to a high demand for successful knee replacement operations.

So-called total knee replacement (TKR) surgery involves replacing the ends of the femur and tibia with prosthetic femoral and tibial components. In some cases, the patella is also replaced with a patella component. During surgery, the patient's femur and tibia are resected, using appropriate cutting instruments, to the form required for mating with the respective femoral and tibial components.

The tibial component of a knee prosthesis typically comprises a plateau with a distal surface configured for mating with a resected proximal end of a tibia and a locating stem extending from the distal surface for insertion into the medullary canal of the tibia.

Such a tibial component is usually cemented on to the proximal end of the tibia and a bearing component is provided on the proximal surface of the plateau to provide an articulating surface for cooperation with the femoral component.

The femoral component of a knee prosthesis is generally C-shaped with the external surface including medial and lateral condyles, which constitute articulating surfaces.

The internal surface of the femoral component is usually constituted by a series of five planar surfaces angled successively. Thus, the resecting of the patient's femur must include the creation of corresponding planar surfaces to mate with those of the femoral component. In order to obtain such planar surfaces, a cutting guide is placed adjacent the distal end of the femur and cutting blades are inserted through appropriately angled slots in the guide.

Traditional instruments and techniques rely upon the surgeon's judgment as to whether the cutting guide is a) located in the correct anterior-posterior position with respect to the femur, and b) located in the correct rotational alignment with the femur. Mal-alignment of the cutting guide in either of these capacities will lead to incorrect location of the femoral component. This may lead to patient discomfort and poor performance of the joint. More specifically, if the cutting guide is located too far in the anterior direction, at least a portion of the anterior cuts will extend beyond the femur so that the resulting planar surface will be shorter than desired and the femoral component will be loose fitting. If the cutting guide is located too far in the posterior direction, the cuts will result in a divot or notch in the femur, which may lead to supracondylar fracture of the femur. Furthermore, if the cutting guide, and therefore the femoral component, is rotationally mal-aligned, the collateral ligaments may not be under the correct tension.

During TKR surgery it is important to obtain a flexion gap, i.e. the distance between the posterior femoral condyles and the proximal tibial surface when the knee is bent by 90 degrees, which is equal to the extension gap, i.e. the distance between the distal femoral surface and the proximal tibial surface when the leg is straight. Usually, the extension gap is measured first and the flexion gap is then matched to the measured extension gap.

It is also important that the collateral ligaments and other soft tissue structures on either side of the knee are placed under the correct tension. Ideally, the lateral and medial collateral ligaments (more correctly, the medial collateral ligament complex and the lateral collateral ligament complex) and soft tissue structures are placed under the same tension. If these ligaments and structures are not under equal tension the patient will have a feeling of instability and there is an increased risk that the bearing parts of the TKR will dislocate. A particular type of dislocation that may occur in mobile bearing designs is known as rotational spin out.

Conventionally, the desired tension of the lateral and medial collateral ligament complexes and soft tissue structures is achieved through the use of two independent distraction devices, each acting between one of the medial and lateral condyles and the proximal tibial surface. Such distraction devices are usually employed in spinal surgery and are large, heavy and cumbersome devices. Since they are operated independently there is a risk that the collateral ligaments and soft tissue structures on the medial and lateral sides of the knee will be unequally tensioned. Reliance is therefore placed on the surgeon to distract equally on both sides. In addition, these distraction devices require a significant amount of effort by the surgeon to operate since they generally involve lever-operated crank mechanisms. Furthermore, it is not uncommon for such devices to hinder access to the knee, during an operation. Moreover, these distraction devices tend to extend outside of the operating field of view so that their use is inconvenient.

An alternative distraction technique involves the use of L-shaped spacers that are successively inserted between the cutting guide and tibia to increase the distance there-between. These only provide for step-wise rather than continual adjustment and they are awkward to use. In addition, to achieve an accurate tensioning with this technique it is necessary for the cutting guide to be held in fixed relationship with the femur. An inaccurate tensioning may therefore be provided if the cutting guide is not held in the correct fixed position.

A consequence of the above is that several large trays of instruments, typically 4-7, are required in TKR procedures. This results in the need to transport and autoclave a large number of devices before each operation.

The instrumentation described in detail in GB2445620B aims to address many of the shortcomings of the above by providing an intramedullary rod for insertion into an end of a femur; a distraction device coupleable to the intramedullary rod and operable between the intramedullary rod and a tibia for adjusting the tension of the collateral ligaments on either side of the knee; and a device for coupling the distraction device to the tibia wherein the device permits adjustment of the position of the distraction device in the anterior and posterior directions of the tibia.

However, as described in GB2445620B, individual block spacers are commonly used to position the cutting guide and/or femoral component, both in TKR procedures and in uni-compartmental knee replacements (also known as partial knee replacements), in which only part of the knee is replaced.

It is possible to effect balanced resection of the posterior condyles during TKR. With the instruments described in GB2445620B (and most other knee instruments), the proximal surface of the tibia is first cut with an external alignment guide and the distal femur is cut using an intramedullary guide. However, neither of these cuts take into account collateral ligament tension or the gap left by bony resection of the tibia and femur. Commonly the surgeon has to release collateral ligaments on the tight side of the knee and use different thicknesses of polyethylene tibial bearings or spacers to fill the gap between the cut ends of the femur and tibia. A major disadvantage of this technique is that when release of the collateral ligament complex on the tight side is performed resulting in a rectangular extension space, that extension space height is variably enlarged and any knee system inserted following release has to fill the variable space created. In older knee systems like GB2445620B and many others, the height of the spacer instruments and each size of polyethylene bearing insert come in 2.5 mm increments. However, in more modern knee replacement systems, the height of each size of spacer instrument and each size of polyethylene bearing insert comes in 1 mm increments giving a massive instrument and implant inventory and increased cost. The same thickness of spacers that have been found to confer stability in extension must also be inserted in flexion and the instruments described in GB2445620B use the intramedullary rod to help position the cutting guide on the spacers.

However, there is a particular downside of inserting an intramedullary rod in that much fat and marrow is driven off into the circulation and this can have deleterious effects. It has been found on a large national level study that total knee replacement has a higher death rate than uni-compartmental knee replacements and fat and marrow embolism are thought to be contributing factors to the higher death rate with TKR.

It is therefore an aim of the present invention to provide a multifunctional spacer for knee surgery that helps to ameliorate the above problems.

SUMMARY OF THE INVENTION

In accordance with a first aspect of the invention there is provided a multifunctional spacer for knee surgery comprising:
a main body configured for use with a single femoral condyle and having an anterior portion of a first height and a posterior portion of a second height, wherein the second height is greater than, equal to or less than the first height; and
wherein the anterior portion and/or the posterior portion is provided with an attachment mechanism for selective attachment of a height adjuster.

Thus, embodiments of present invention provide a multifunctional spacer for use with a single condyle and which can be configured to provide two or more different heights for increased flexibility. Accordingly, a smaller inventory of spacers can be provided to cover a large range of different heights and height adjusters can be attached as required for different purposes. The spacers and height adjusters can be used to provide balanced resection in both extension and flexion. Furthermore, the spacers can be used during knee surgery so as to avoid the need for an intramedullary rod, as will be described in more detail below.

The posterior portion of a first spacer may be configured (i.e. of an appropriate size and shape) for insertion between a trial tibial component and a medial femoral condyle and the posterior portion of a second spacer may be configured (i.e. of an appropriate size and shape) for insertion between a lateral side of the trial tibial component and a lateral femoral condyle when the knee is in extension, to obtain a desired amount of collateral ligament tension prior to a distal femoral resection. Notably, the posterior portions of the first and second spacers may have differing thicknesses.

The posterior portion of a first spacer may be configured (i.e. of an appropriate size and shape) for insertion between a trial tibial component and the medial femoral condyle and the posterior portion of a second spacer may be configured (i.e. of an appropriate size and shape) for insertion between a lateral side of the trial tibial component and the lateral femoral condyle when the knee is in flexion, to obtain a desired amount of collateral ligament tension prior to further femoral resection. Notably, the posterior portion of the lateral spacer may be thicker that the posterior portion of the medial spacer.

The anterior portion of the spacer may be configured to support a cutting block for use by the surgeon when making one or more femoral cuts during femoral resection when the knee is in flexion.

The posterior portion may have a thickness of, for example, 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm or 20 mm. In use, however, it has been found that 1 mm increments from 3 mm to 13 mm are usually satisfactory for knee replacement surgery.

The anterior portion may have a thickness of, for example, 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm or 20 mm. In use, however, an anterior thickness of 6 mm has been found to be satisfactory for knee replacement when the thickness of a tibial trial baseplate is 4 mm. In some embodiments, the thickness of the anterior portion is designated as a total thickness of a tibial baseplate plus a minimum thickness of a polyethylene tibial bearing surface and, in this embodiment, the spacers are placed on a cut surface of the upper tibia rather than on the trial tibial baseplate. Most known knee replacements have a minimum thickness tibial component (including a tibial baseplate and a tibial bearing surface) of 10 mm. In which case, the designated total thickness of the anterior portion will be 10 mm although an actual thickness of the anterior portion will be 10 mm minus the thickness of the tibial baseplate. For example, if the tibial baseplate is 4 mm thick, the anterior portion will have an actual thickness of 6 mm to provide a designated thickness of 10 mm in total.

The attachment mechanism may comprise one or more sockets on the spacer and one or more complementary plugs on the height adjuster.

The multifunctional spacer may comprise one or more height adjuster. The height adjuster may have a thickness of, for example, 1 mm, 2 mm, 2.5 mm, 5 mm, 7.5 mm or 10 mm.

The height adjuster may have a bearing surface that is substantially rectangular, substantially circular, substantially L-shaped, substantially U-shaped, substantially V-shaped, substantially O-shaped or otherwise.

In some embodiments, the posterior portion will have an attachment mechanism for a posterior height adjuster and/or the anterior portion will have an attachment mechanism for an anterior height adjuster.

The posterior height adjuster and the anterior height adjuster may be the same or different in shape or thickness so as be easily distinguished from one another. Furthermore, the attachment mechanism on the posterior portion and the attachment mechanism on the anterior portion may be different to only permit attachment of the posterior height adjuster or the anterior height adjuster, respectively.

The spacer and/or the height adjuster may be formed from plastic, metal, ceramic or other suitable materials.

In accordance with a second aspect of the invention there is provided a pair of multifunctional spacers according to the first aspect, wherein the posterior portion of a first spacer is configured (i.e. of an appropriate size and shape) for insertion between a trial tibial component and a medial femoral condyle and the posterior portion of a second spacer is configured (i.e. of an appropriate size and shape) for insertion between a trial tibial component and a lateral femoral condyle, when the knee is in extension, to obtain a desired amount of collateral ligament tension on both medial and lateral sides of a knee prior to a distal femoral resection.

In addition, the posterior portion of the first spacer may be configured (i.e. of an appropriate size and shape) for insertion between the trial tibial component and the medial femoral condyle and the posterior portion of the second spacer may be configured (i.e. of an appropriate size and shape) for insertion between the trial tibial component and the lateral femoral condyle, when the knee is in flexion, to obtain a desired amount of collateral ligament tension on both medial and lateral sides of the knee prior to further femoral resection.

In accordance with a third aspect of the invention there is provided a kit of multiple multifunctional spacers according to the first aspect of the invention, wherein the posterior portion of each multifunctional spacer has a different thickness.

At least one height adjuster may be included in the kit.

A fourth aspect of the invention relates to use of multifunctional spacers according to the first aspect of the invention, during knee surgery, wherein the posterior portion of a first spacer is inserted between a trial tibial component and a medial femoral condyle and a posterior portion of a second spacer is inserted between the trial tibial component and a lateral femoral condyle in both extension and when the knee is flexed to 90 degrees, so as to obtain balanced femoral resection creating a pre-determined space for knee components. In particular, the pre-determined space may be configured for utilising 10 mm thick polyethylene bearing components in nearly every case, thus minimising inventory and costs for surgery.

One or more height adjusters may be attached to the posterior portion and/or the anterior portion of at least one of the spacers during use.

BRIEF DESCRIPTION OF THE DRAWINGS

Embodiments of the invention will now be described, by way of example only, with reference to the drawings in which:

FIG. 3b shows a multifunctional spacer of FIG. 2 including the posterior height adjuster of FIG. 3a;

DETAILED DESCRIPTION

Figure 1:
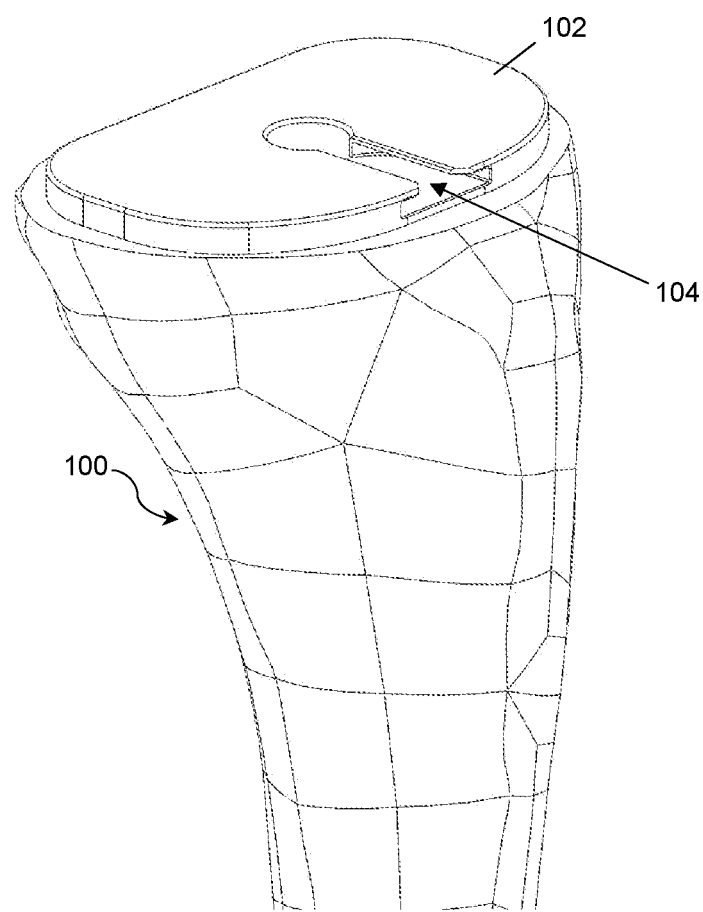
FIG. 1 shows a resected tibia fitted with a trial tibial baseplate in accordance with an embodiment of the invention.

FIG. 1 shows a first step in a total knee replacement procedure, in accordance with embodiments of the invention. Notably, a surgeon may utilise tools such as those described above and in GB2445620B without significantly altering his/her surgical technique.

Figure 5:
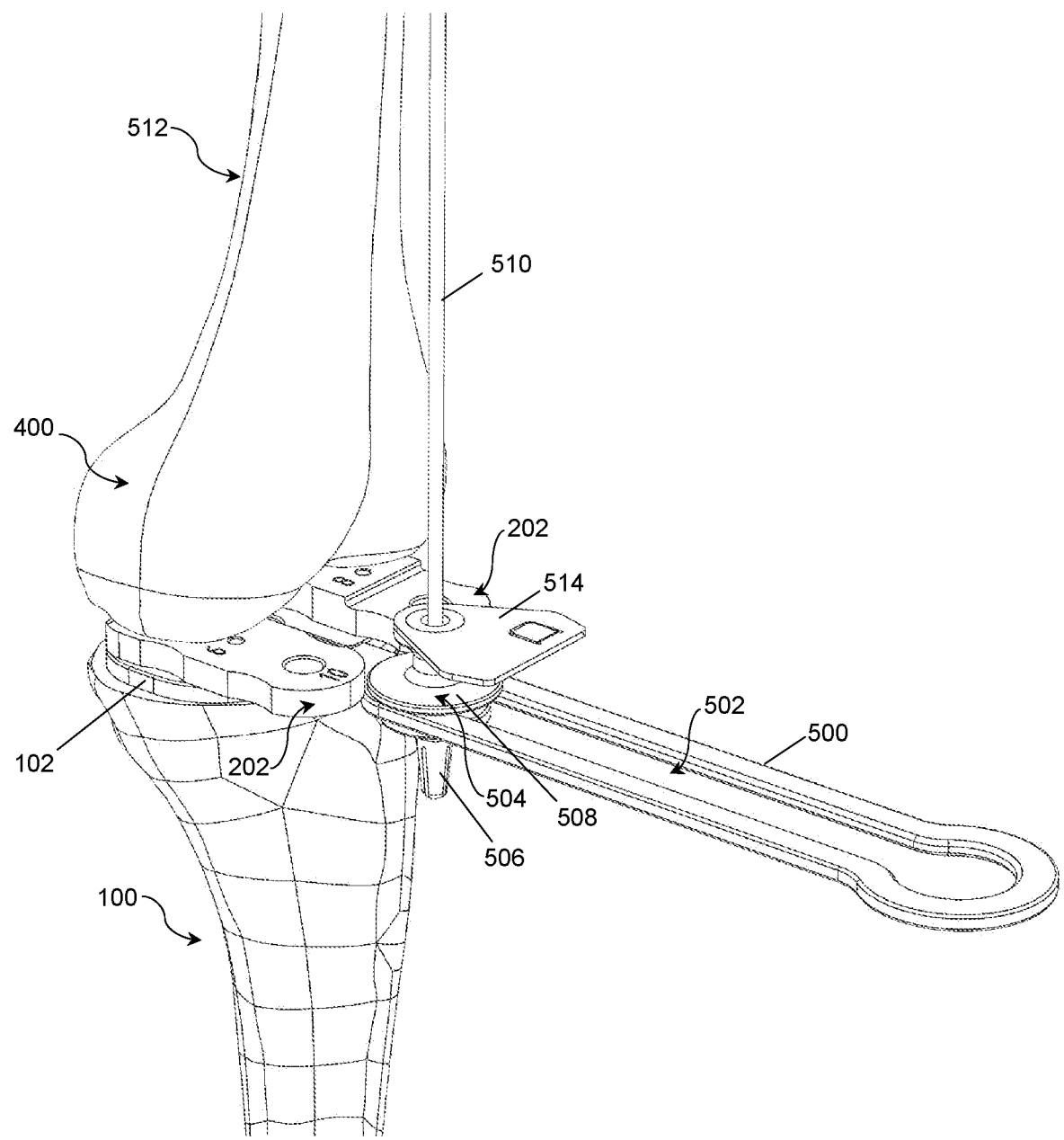
FIG. 5 shows a view similar to that of FIG. 4 but with an alignment arm fitted to the trial tibial baseplate, a leg alignment tool fitted to the alignment arm, an external alignment rod fitted to the leg alignment tool and a distal femoral cutting guide fitted to the leg alignment tool, in accordance with an embodiment of the invention.

As shown in FIG. 1, a proximal arthritic surface of a tibia 100 has been resected and fitted with a trial tibial component in the form of a trial tibial baseplate 102. The resection may be performed using an extra-medullary guide, an intramedullary guide, a custom tibial cutting guide, a navigation-assisted tibial cutting guide or a robot-assisted tibial cutting guide. Known knee-specific surgical instruments are used to prepare the proximal surface of the tibia 100 before the trial tibial baseplate 102 is inserted. In this particular embodiment, the trial tibial baseplate 102 is similar to that described in GB2445620B but further includes a radial anterior slot 104 which is configured for receipt of an alignment arm as shown in FIG. 5 and described in more detail below.

Figure 2:
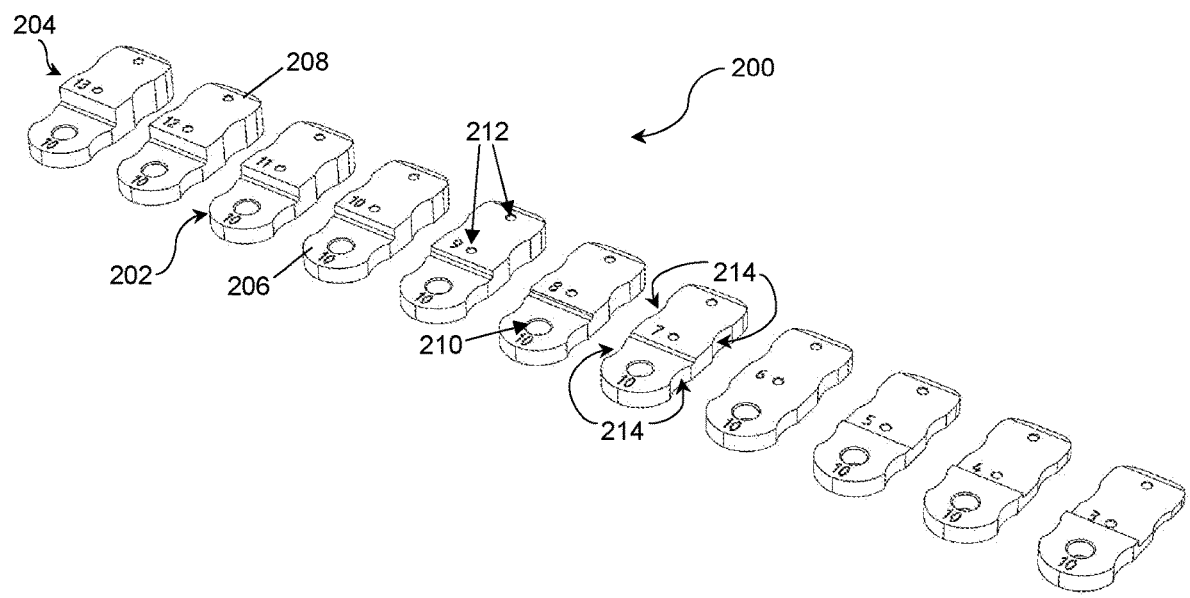
FIG. 2 shows a kit of eleven multifunctional spacers in accordance with an embodiment of the invention.

FIG. 2 shows a kit 200 of eleven multifunctional spacers 202 in accordance with embodiments of the invention. Each spacer 202 comprises a main body 204 in plastic having an anterior portion 206 of a first height and a posterior portion 208 of a second height, wherein the second height is greater than, equal to or less than the first height. In the kit 200, each anterior portion 206 has a height of 6 mm although it is designated as 10 mm to account for a thickness of 4 mm for the trial tibial baseplate 102. The posterior portions 208 all vary in height in 1 mm increments from 3 mm to 13 mm. It will be understood that in other embodiments, different heights and/or different increments may be employed.

Each anterior portion 206 is provided with an attachment mechanism 210 in the form of a relatively large cylindrical socket for selective attachment of an anterior augmentable height adjuster as will be described below and each posterior portion 208 is provided with two attachment mechanisms 212 in the form of relatively small cylindrical sockets for selective attachment of a posterior augmentable height adjuster as will be described below. In addition, each anterior portion 206 and each posterior portion 208 has opposed sides including grooves 214 shaped for gripping by a surgeon's fingers or by a tool during insertion and removal.

Figure 3A:
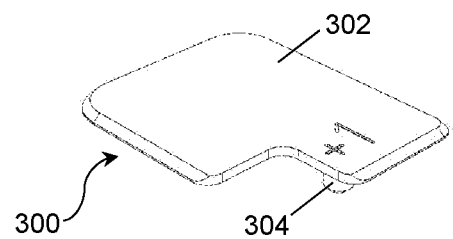
FIG. 3a shows a posterior height adjuster in accordance with an embodiment of the invention.

FIG. 3a shows a posterior augmentable height adjuster 300 of 1 mm thickness metal, in accordance with an embodiment of the invention. The posterior augmentable height adjuster 300 has a bearing surface 302 that is substantially L-shaped so as to not obscure a height indication provided on the posterior portion 208 of the spacer 202 when fitted thereon. An underside of the posterior augmentable height adjuster 300 is provided with two cylindrical posts 304 for insertion into the attachment mechanisms 212 to secure the posterior augmentable height adjuster 300 on the spacer 202.

Figure 3B:
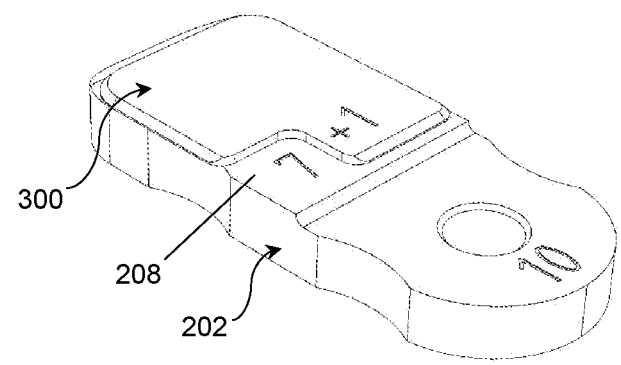

FIG. 3b shows one multifunctional spacer 202 of FIG. 2 having fitted to the posterior portion 208, the posterior augmentable height adjuster 300 of FIG. 3a. In this case, the multifunctional spacer 202 has a posterior portion 208 with a height of 7 mm, which is increased to a total height of 8 mm with inclusion of the posterior augmentable height adjuster 300. In this case, the posterior augmentable height adjuster 300 is snap-fitted onto the posterior portion 208. However, in other embodiments, other types of attachment mechanisms may be employed.

The provision of the posterior augmentable height adjuster 300 means that the number of spacers 202 provided in the kit 200 can be halved since, if a same thickness of spacer 202 is required on a medial and a lateral side of the knee, the posterior augmentable height adjuster 300 can be fitted to a spacer 202 having a smaller posterior portion 208 to increase its height.

Figure 4:
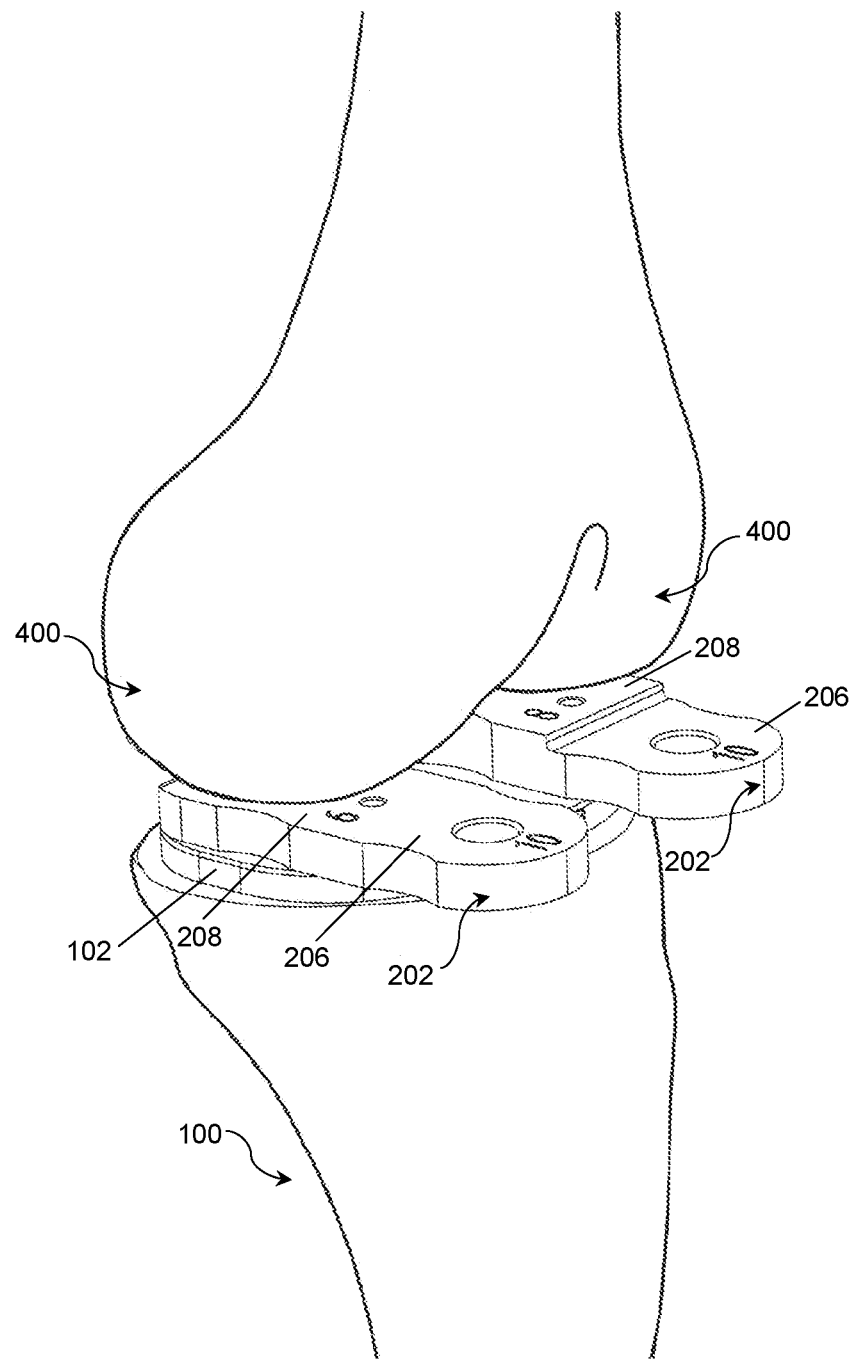
FIG. 4 shows the resected tibia of FIG. 1 in extension, with two of the multifunctional spacers of FIG. 2 inserted between the trial tibial baseplate and femoral condyles.

FIG. 4 shows the resected tibia 100 of FIG. 1 with the knee in full extension (i.e. when the leg is straight), with two of the multifunctional spacers 202 of FIG. 2 inserted in situ between the trial tibial baseplate 102 and femoral condyles 400. More specifically, one spacer 202 is provided with its posterior portion 208 between a top surface of the trial tibial baseplate 102 and a medial femoral condyle 400 and one spacer 202 is provided with its posterior portion 208 between the trial tibial baseplate 102 and a lateral femoral condyle 400. Each anterior portion 206 extends forwardly of the knee for a later use as will be described below.

Before insertion of the spacers 202, osteophytes on an edge of the femoral condyle 400 and tibial plateau on a worn side of the knee are resected. These osteophytes mean that the collateral ligaments make a C-shape around the osteophytes and are effectively shortened. Different thicknesses of spacers 202 are therefore tried to space the components such that the collateral ligament tension is neither too tight nor too lax.

In this case, the posterior portion 208 adjacent the medial condyle 400 is 6 mm thick and the posterior portion 208 adjacent the lateral condyle 400 is 8 mm thick. No posterior augmentable height adjusters 300 are required in this instance, however, one could be used along with a 5 mm posterior portion 208 to provide the 6 mm thickness for the medial condyle 400 and one could be used along with a 7 mm posterior portion 208 to provide the 8 mm thickness for the lateral condyle 400. Similarly, if both spacers 202 were required with the same thickness, a posterior augmentable height adjuster 300 could be used on one of the spacers 202 which is 1 mm less thick than the other spacer 202 to bring it back to the same height as the other spacer 202. Thus, only a single set or kit of different thickness spacers 202 is required for each knee, not for each condyle.

Once the spacers 202 are inserted as per FIG. 4, a distal femoral resection is performed by measuring up from the trial tibial baseplate 102 as illustrated in FIG. 5. In this embodiment, an alignment arm 500 is inserted into the radial anterior slot 104 on the front of the trial tibial baseplate 102 and extends in a radial anterior direction. The alignment arm is generally planar and includes a central longitudinal slot 502 for sliding engagement with a leg alignment tool 504. The leg alignment tool 504 includes a depending peg 506 and a circular disc 508 which has a circumferential groove arranged such at the leg alignment tool 504 is slideably engaged in the central longitudinal slot 502. An external alignment rod 510 is fitted to the leg alignment tool 504 and extends along the length of a femur 512. A distal femoral cutting guide 514 is fitted to a top of the leg alignment tool 504. The distal femoral cutting guide 514 is of a generally planar triangular shape and is configured to rotate about the external alignment rod 510 so that it can be moved close to or away from the femoral condyles 400.

Before a patient's leg is sterilised and surgically draped a palpable marker is attached to the patient's skin over the femoral artery as the position of the femoral artery pulsation equates to a centre of the femoral head.

Figure 6:
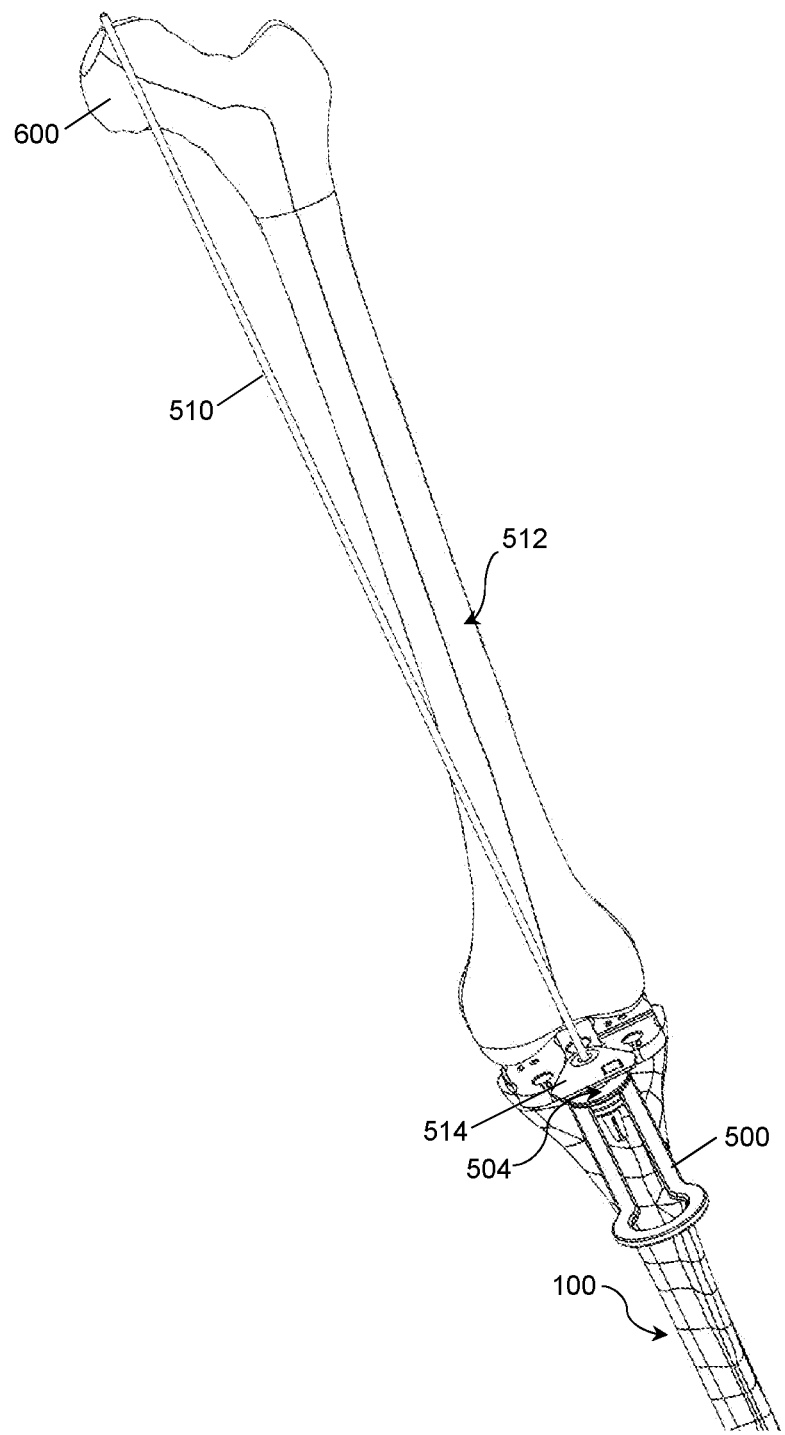
FIG. 6 shows a view of the set-up of FIG. 5 including a top of the femur and a top of the external alignment rod.

FIG. 6 shows a view of the set-up of FIG. 5 including a top of the femur 512 and a top of the external alignment rod 510 which is located such it lies over the centre of the femoral head 600 as indicated by the palpable marker. In other embodiments, a laser pointer or light pen can be utilised instead of an external alignment rod.

It is noted that normal alignment of a leg has the centre of the femoral head 600, centre of the knee joint and centre of the ankle joint connected by a straight line. If alignment of the leg is not correct at this stage then tight soft tissues are sequentially released as is known in all knee replacement procedures to achieve correct leg alignment. When satisfactory leg alignment has been achieved, the external alignment rod 510 is removed.

Figure 7:
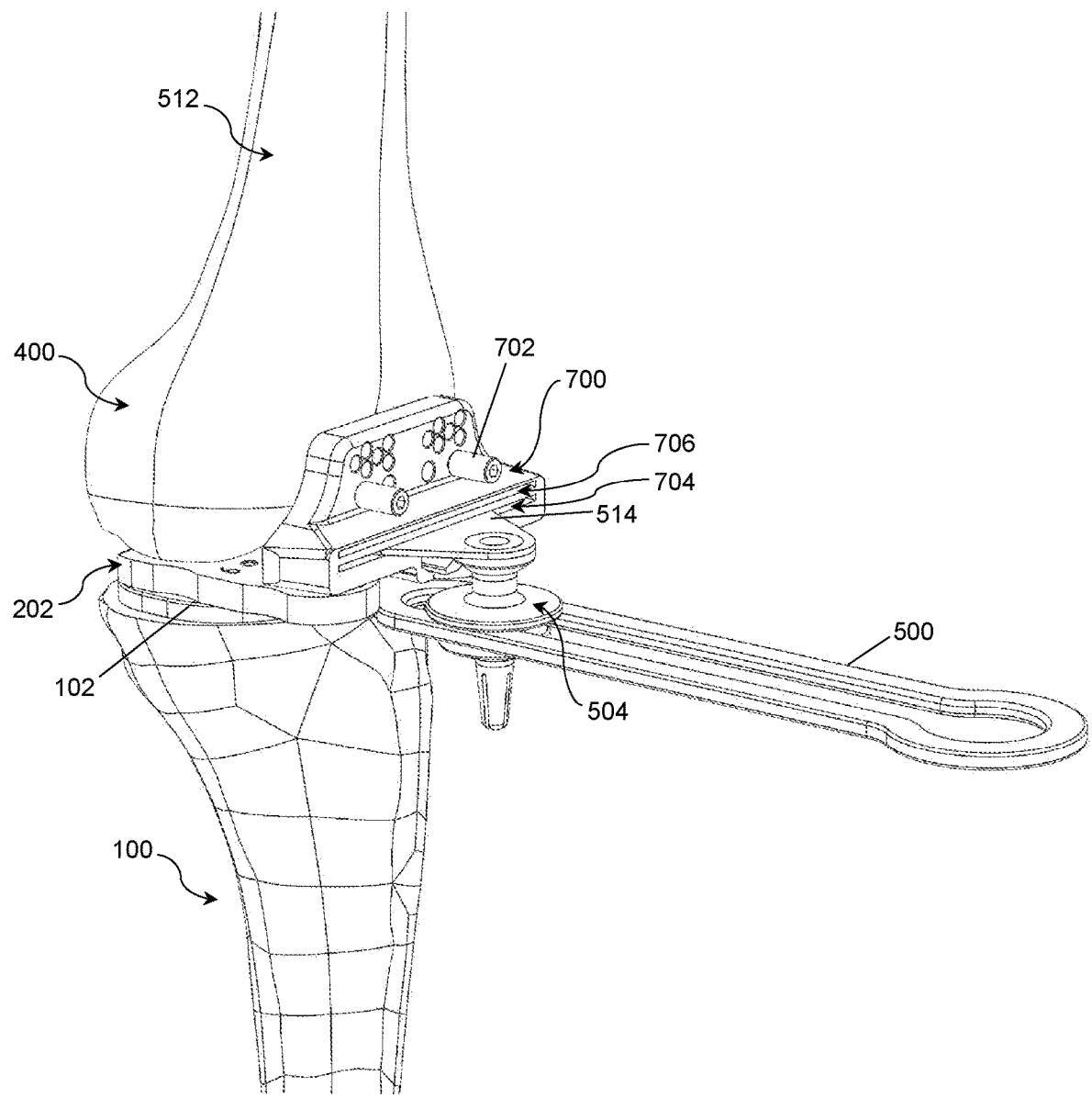
FIG. 7 shows a view similar to that of FIG. 5 but with the external alignment rod removed and a distal femoral cutting block coupled to the distal femoral cutting guide.

FIG. 7 shows the leg alignment tool 504 and the distal femoral cutting guide 514 being used to position a distal femoral cutting block 700. The distal femoral cutting block 700 does not contact the anterior portions 206 of each spacer 202. The distal femoral cutting block 700 is fixed with screws 702 in this case, although pins or other fastenings could be used to lock the distal femoral cutting block 700 to the anterior of the femur 512. The distal femoral cutting block 700 has a distal slot 704 and a proximal slot 706, each of which can be used as appropriate to make a distal femoral cut.

First, an assessment is made as to whether the distal slot 704 in the distal femoral cutting block 700 is going to cut a satisfactory amount of bone from the distal end of the femur 512 so that sufficient bone support for a definitive femoral implant will be achieved. Under normal circumstances, a cut through the distal slot 704 will be satisfactory but where there the patient has rarely stretched ligaments or marked bone loss, a more proximal cut on the distal end of the femur 512 is necessary.

Thus, under normal circumstances a cut through the distal slot 704 will leave correct spacing for the thickness of a distal femoral component of the implant, the thickness of a spacer 202 and the thickness of the trial tibial baseplate 102 (e.g. 10 mm). At the same time collateral ligament tension and leg alignment will be normal. However, in unusual circumstances, if a correct amount of bone is not going to be resected from the distal end of the femur 512 by cutting through the distal slot 704, then the proximal slot 706 on the distal femoral cutting block 700 is used and a thicker spacer 202 (e.g. 12.5 mm) is used. In extreme circumstances, if sufficient bone is not going to be removed from the distal end of the femur 512 by using the proximal slot 706, then the distal femoral cutting block 700 is moved more proximally and a distal femoral cut to accommodate an even thicker spacer 202 (e.g. 15 mm or 17.5 mm) is used.

Figure 8:
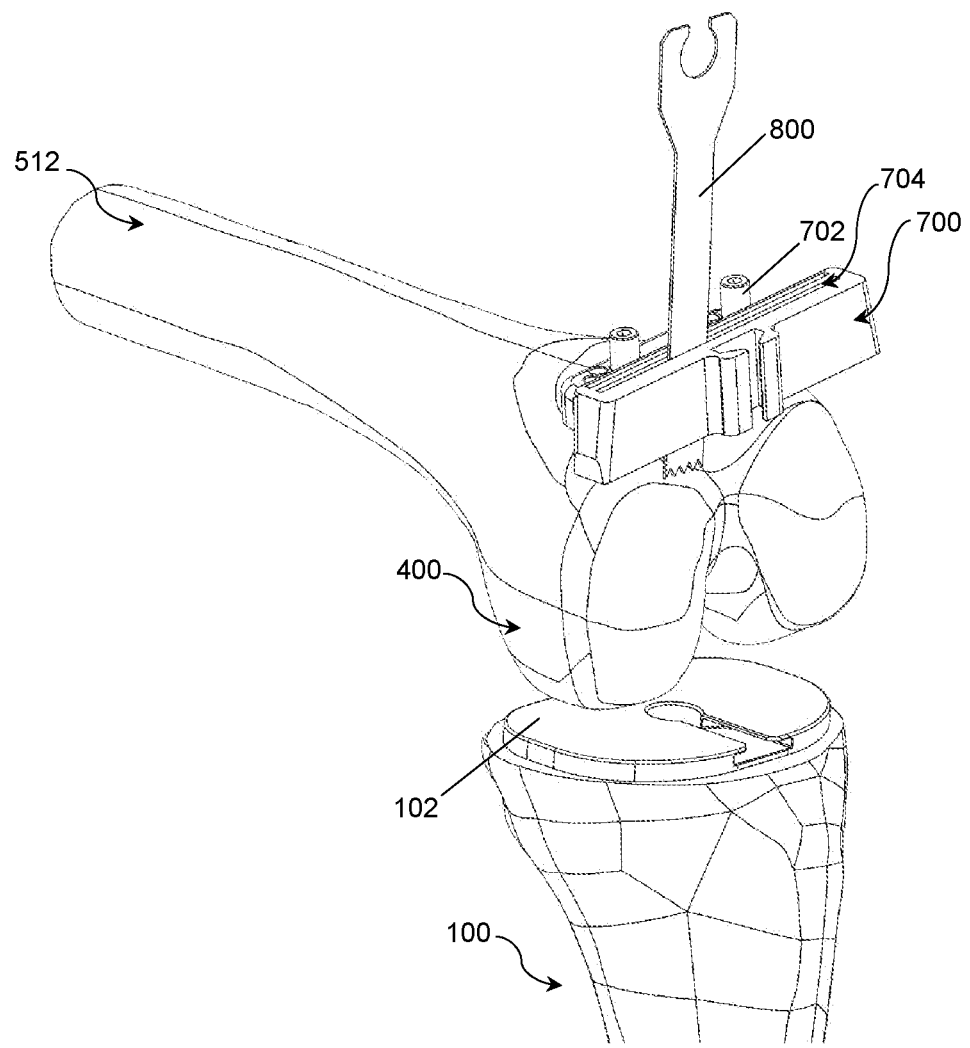
FIG. 8 shows the knee in 90 degree flexion and a saw being used through the distal femoral cutting block for the distal femoral resection.

FIG. 8 shows the knee in 90 degree flexion and a saw 800 being used through the distal slot 704 in the distal femoral cutting block 700 for the distal femoral resection of both the medial and lateral condyles 400. The spacers 202 may be removed while the cuts are being made. Once the distal end of the femur 512 has been resected, the distal femoral cutting block 700 is removed by unscrewing the screws 702.

Figure 9:
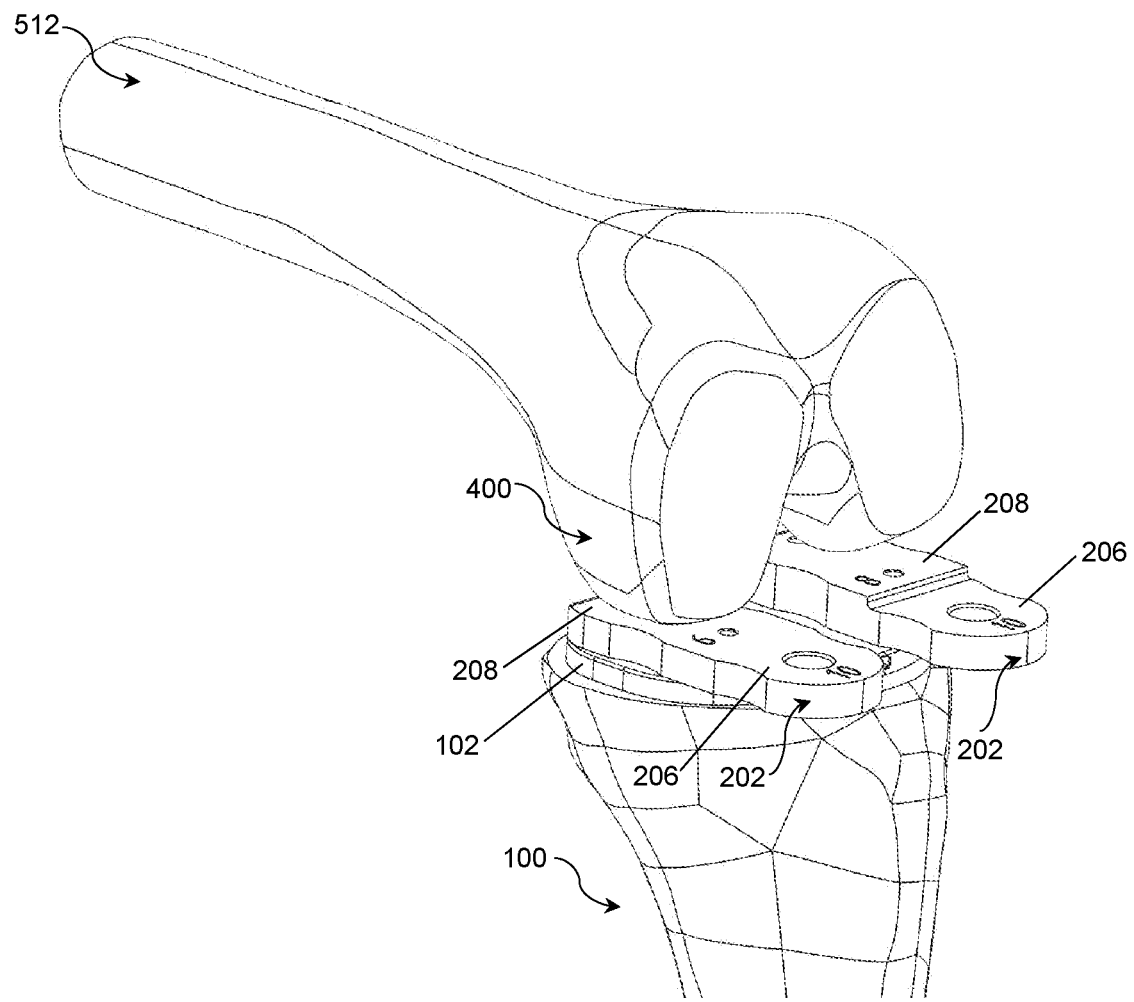
FIG. 9 shows the knee in 90 degree flexion, after the distal femoral resection, and wherein two of the multifunctional spacers of FIG. 2 are inserted between the tibial baseplate and a posterior of the femoral condyles.

FIG. 9 shows the knee in 90 degree flexion, after the distal femoral resection, and wherein two of the multifunctional spacers 202 of FIG. 2 are inserted between the trial tibial baseplate 102 and a posterior of the femoral condyles 400. As before (when the knee was in extension), in this embodiment, a thicker spacer 202 (8 mm) is used between the lateral femoral condyle 400 and the trial tibial baseplate 102 than is used between the medial femoral condyle 400 and the trial tibial baseplate 102 (6 mm). However, in general, the medial and lateral spacer thickness in flexion has no relationship to the two spacer thicknesses used in extension. The only factor governing thickness of each spacer is collateral ligament complex tension on each of the medial and lateral sides, both in extension and in flexion.

The spacers 202 are inserted into the medial and lateral compartments of the knee to tension the soft tissues in flexion (i.e. with the knee bent). A typical situation is that a 5 mm posterior thickness spacer 202 will be suitable on the medial side and an 8 mm posterior thickness spacer 202 will be good for soft tissue tension on the lateral side. This is a welcome situation for the surgeon as the femoral component of the implant will be inserted with approximately 3 degrees of external rotation which is the accepted norm for femoral component positioning during rotation. However, the surgeon must be alert to the possibility that huge variation might occur following insertion of the spacers 202. For example, if a 3 mm spacer 202 on the medial side gives satisfactory soft tissue tension on the medial side but a 13 mm spacer 202 is required to give satisfactory soft tissue tension on the lateral side, this would place the femoral component in too much external rotation. The pathological setup that typically causes this is gross medial compartment arthritis with osteophyte at the back of the medial femoral condyle with tenting and contracture of the postero-medial joint capsule. The surgeon should resect posterior osteophytes and, if necessary, release the postero-medial capsule to allow thicker spacers 202 on the medial side, which more closely match those on the lateral side to provide more normal rotation of the femoral component.

Thus, in flexion, the posterior portions 208 of the spacers 202 are used to ensure balanced collateral tension so that normal rotation of the femoral component is permitted. In addition, the anterior portions 206 of the spacers 202 are used to position a further (four-in-one) femoral cutting block, as will be described in more detail below.

Figure 10:
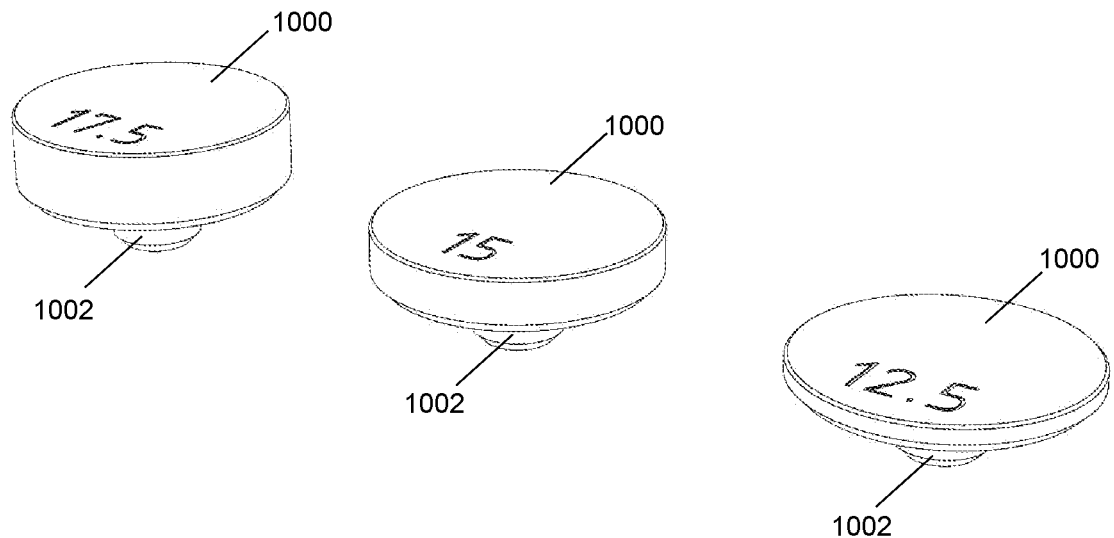
FIG. 10 shows three anterior height adjusters in accordance with an embodiment of the invention.

FIG. 10 shows three anterior augmentable height adjusters 1000 which may be used on the anterior portion 206 of a spacer 202 to change its height for correct positioning of the further femoral cutting block. The anterior augmentable height adjusters 1000 comprise cylindrical metal discs and are, respectively, 2.5 mm, 5 mm and 7.5 mm thick. A central depending stud 1002 is provided for location in the attachment means 210 on the anterior portion 206 of the spacer 202, such that when the anterior augmentable height adjusters 1000 are attached to the spacers, they provide a designated combined height of 12.5 mm, 15 mm and 17.5 mm, respectively (including the height of the anterior portion 206 and the trial tibial component 102).

In use, however, an anterior augmentable height adjuster 1000 may not be required and, in practice, only a single thickness (e.g. 10 mm thick) of tibial bearing components may be required. This is a significant departure from traditional knee replacement techniques which require a large inventory of parts. The conventional technique of cutting the distal femur and top of the tibia ignoring collateral ligament complex tension, then carrying out a release on the tight side to get a rectangular extension gap means that a huge inventory of parts is required to fill the variable height of the extension space. However, using the present technique of balanced resection means that the collateral ligaments are tensioned before the distal femur is resected and, furthermore, the resection can be done to create a gap that is a perfect fit for a desired (i.e. smallest) thickness of tibial polyethylene bearing—both in extension and in flexion. So, instead of the more modern knee systems supplying multiple thicknesses of tibial bearings in 1 mm increments, this present system only requires one thickness of tibial bearings to be provided for an operation (that is, except in the rare cases of severe bone loss/ligament laxity which can be seen on a x-ray long before operation and this can therefore be planned for).

Figure 11:
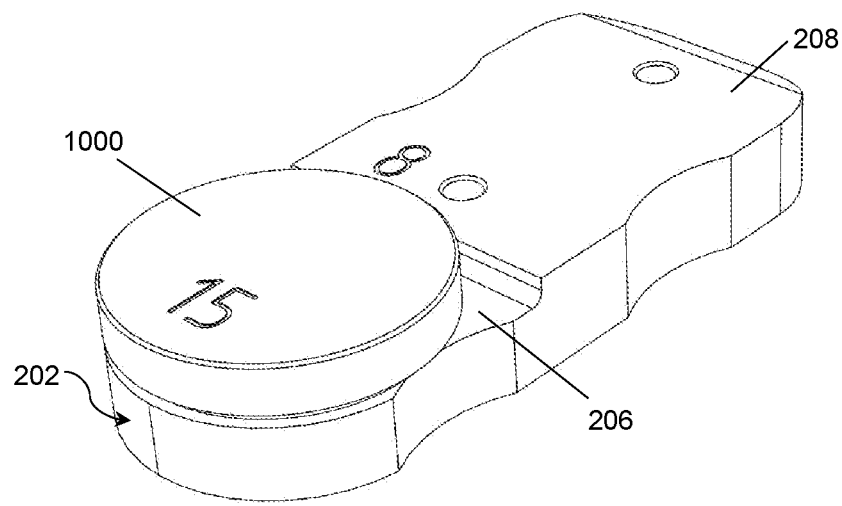
FIG. 11 shows a multifunctional spacer of FIG. 2 including one of the anterior height adjusters of FIG. 10.

FIG. 11 shows a multifunctional spacer 202 of FIG. 2 including one of the anterior augmentable height adjusters 1000 of FIG. 10 on the anterior portion 206 such that the designated height is 15 mm.

It should be noted that the anterior augmentable height adjusters 1000 are only used if a greater amount of distal femur has been resected at an earlier stage than the minimum thickness spacer 202 will accommodate with correct soft tissue tension. Most known knee replacements have a minimum thickness tibial component of 10 mm. That means the thickness of the top surface of the trial tibial baseplate 102 plus the minimum thickness of the spacer should equal 10 mm. In the Birmingham knee replacement (BKR) which the Applicant uses, the thickness of the tibial baseplate 102 is 4 mm and the minimum thickness of the spacer 202 in the anterior portion 106 is 6 mm. However there is huge variability between implant suppliers and one supplier may have a tibial baseplate 102 of 3.74 mm thickness and a minimum spacer 202 thickness of 6.26 mm. Naming a spacer 202 as 6.26 mm thickness and with every supplier's products being slightly different would be confusing for surgeons and operating room staff, so the spacer 202 is given a nominal thickness of 10 mm even though the 10 mm relates to the total thickness of the tibial baseplate 102 plus the minimum thickness of the spacer 202 in the anterior portion 206.

If the distal end of the femur 512 has been resected through the distal slot 704 of the distal femoral cutting block 700, no anterior augmentable height adjusters 1000 are necessary on the anterior portions 206 of the spacers 202 when the knee is in 90 degrees of flexion. Instead, the anterior portions 206 of the spacers 202, which are 6 mm in thickness (10 mm nominal) across all spacers 202 in the kit, are used to position a further (four-in-one) femoral cutting block, as shown in FIG. 12.

Figure 12:
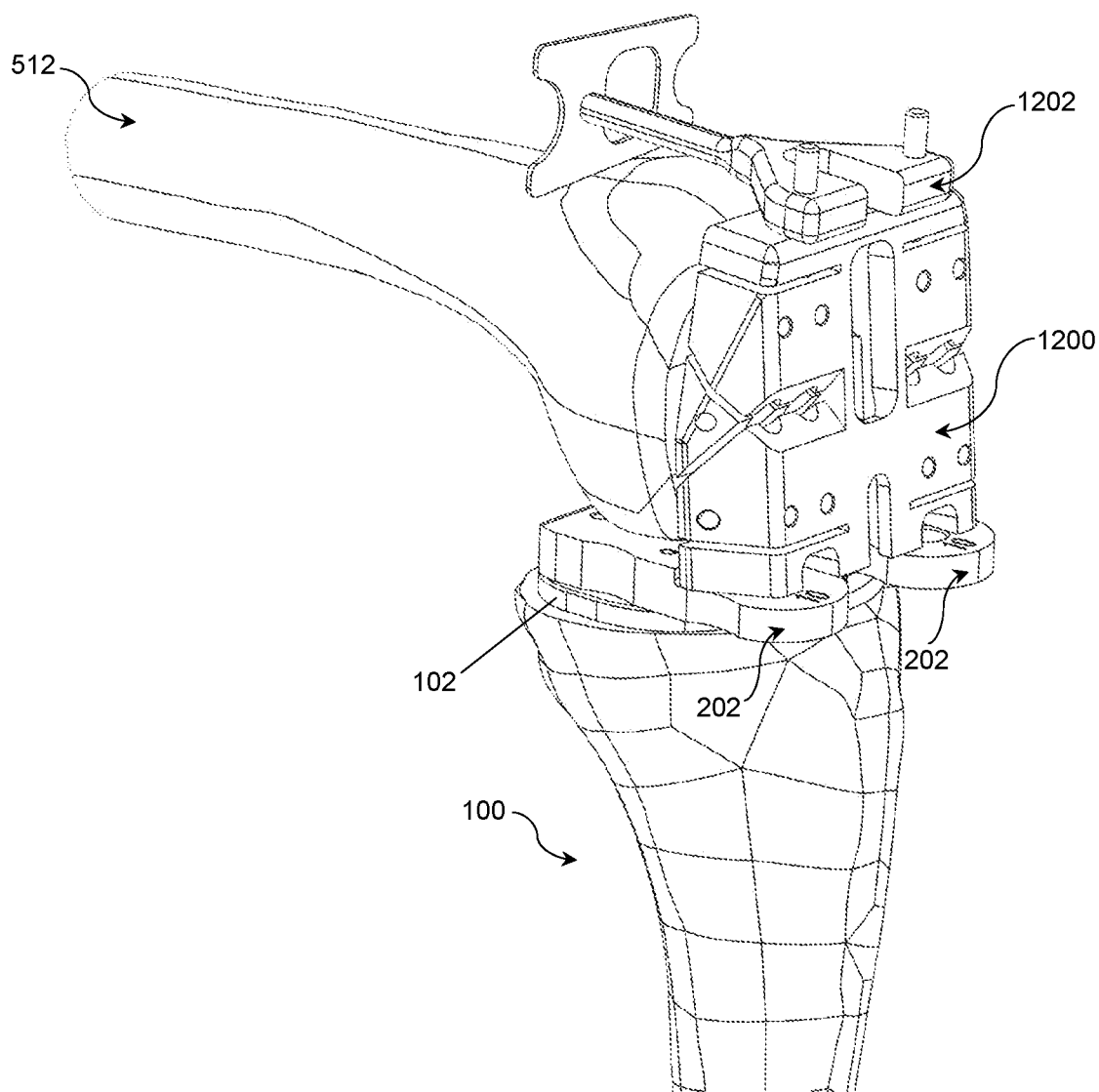
FIG. 12 shows a view similar to that of FIG. 9 but with a cutting block supported by the anterior portions of the multifunctional spacers and a notch guide provided on top of the cutting block.

More specifically, FIG. 12 shows a view similar to that of FIG. 9 but with a further (four-in-one) femoral cutting block 1200 supported by the anterior portions 206 of the multifunctional spacers 202 and a notch guide 1202 provided on top of the cutting block 1200. The cutting block 1200 is similar to that described in detail in GB2445620B and includes several screw holes for attachment to the femur 512 and four different slots through which a surgeon can insert a saw to make cuts to resect the femoral condyles 400. The notch guide 1202 is also similar to that described in detail in GB2445620B and ensures the correct size of cutting block 1200 is employed.

Figure 13:
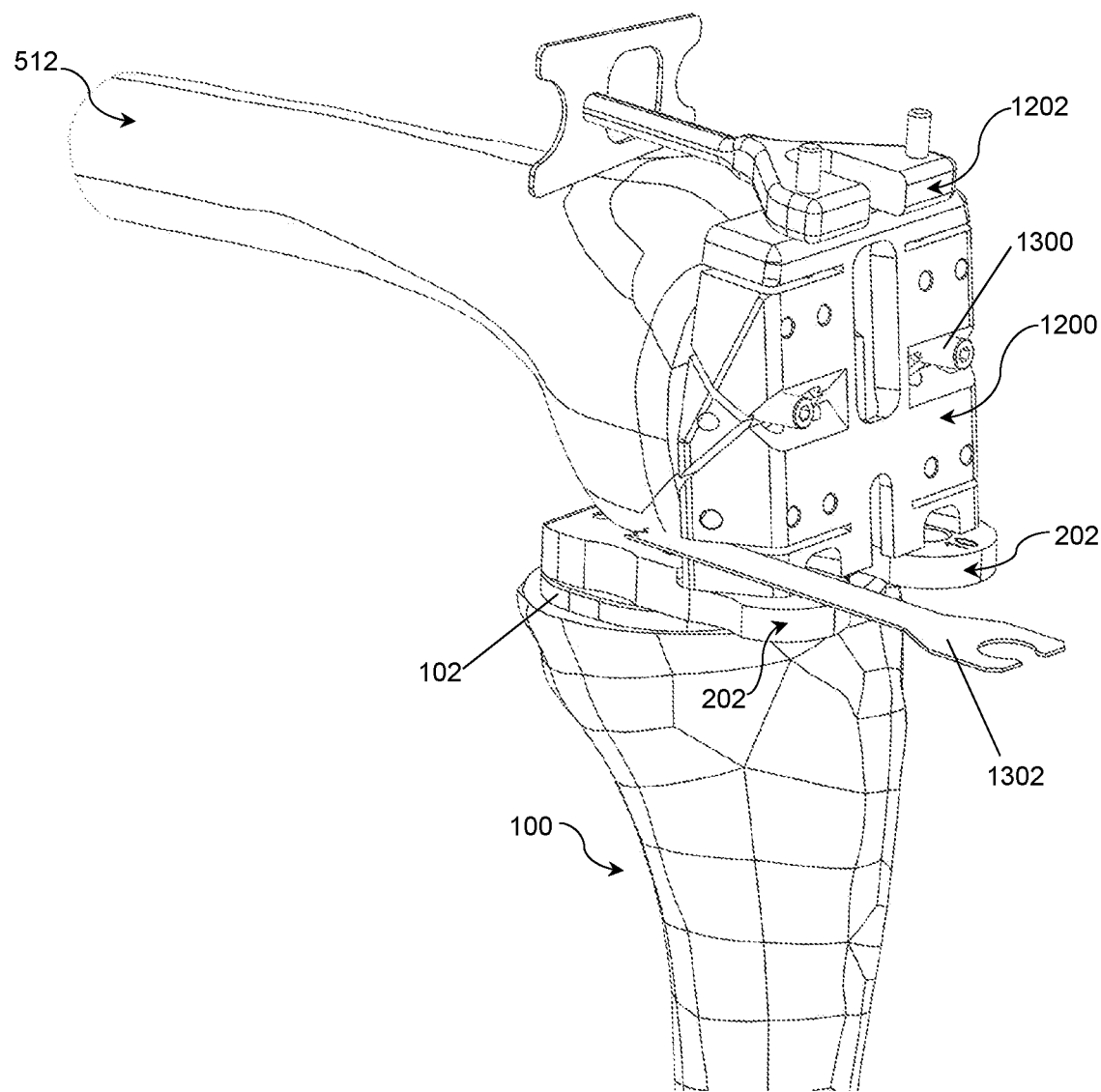
FIG. 13 shows a view similar to that of FIG. 12 but with the cutting block screwed onto the femur and a saw being used through the cutting block for further femoral resection.

There are a range of sizes of femoral components, each corresponding to a particular size of cutting block 1200. If a particular size of cutting block 1200 is too small, then an anterior cut on the femur 512 can notch the front of the femur 512 making it susceptible to fracture. A larger cutting block 1200 is selected that will not result in an anterior femoral notch. When the cutting block 1200 is positioned satisfactorily, it is fixed to the distal end of the femur 512 with screws or pins 1300 as shown in FIG. 13. FIG. 13 also shows a saw 1302 being used through the cutting block 1300 for further femoral resection. In this case, the posterior femoral cut is shown as being made.

A particular feature of the cutting block 1200 is that the thickness of metal below the posterior femoral cut plus the thickness of the saw cut is the same as the thickness of the posterior condyle of the femoral component. Accordingly, using the cutting block 1200 and the spacers 202 when making the posterior femoral cuts will result in the thickness of the posterior condyle of the femoral component plus the minimum thickness of the spacer 202 plus the thickness of the tibial baseplate 102 will fill the space perfectly giving a rectangular and balanced flexion space. This gives the patient a secure knee when flexed with almost no risk of an inter-engaging cam and peg securing the femoral component to the tibial component in use, jumping or providing a feeling of insecurity.

The remaining three cuts on the distal end of the femur 512 are performed in the normal fashion using the remaining slots on the cutting block 1200.

If a greater amount of distal femur 512 has been removed in extension requiring, for example, a 15 mm anterior portion 206 spacer 202, then an appropriate thickness anterior augmentable height adjuster 1000 must be attached to the anterior portion 206 of the spacer 202 in flexion so that soft tissue tension in flexion and extension are the same.

Figure 14:
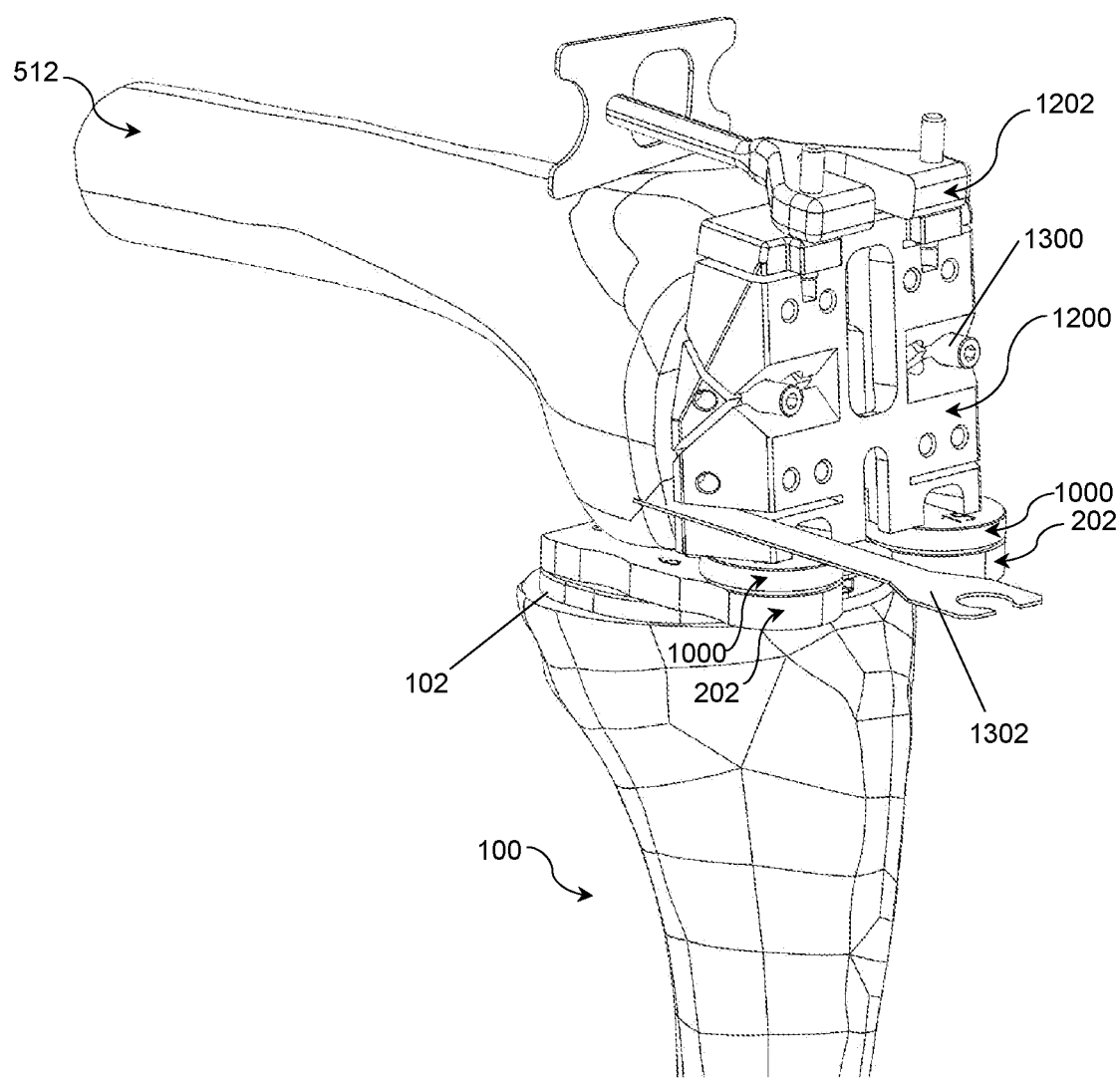
FIG. 14 shows a view similar to that of FIG. 13 but with two anterior height adjusters as shown in FIG. 10, provided on the anterior portions of the multifunctional spacers to support the cutting block.

FIG. 14 shows a view similar to that of FIG. 13 but with two anterior augmentable height adjusters 1000, as shown in FIG. 10, provided on the anterior portions 206 of each multifunctional spacer 202 to support the cutting block 1200 at the correct height when making the femoral cuts.

Once all cuts are made, the femoral component is affixed to the resected femur 512 and the tibial component is affixed to the tibia 100 using known techniques.

Thus, the posterior portions 208 of the multifunctional spacers 202 are used to ensure balanced collateral ligament tension by providing an appropriate spacing between the femoral condyles 400 and the tibia 100, both during extension and during flexion of the knee; and the anterior portions 206 of the multifunctional spacers 202 are used to ensure correct placement of cutting block 1200, during flexion of the knee. Accordingly, a better alignment of the knee is achieved after a total knee replacement and as no intramedullary rod is required in the above procedure, the risk of death associated with its use is eliminated.

Although only certain embodiments of the present invention have been described in detail, many variations are possible in accordance with the appended claims. For example, features described in relation to one embodiment may be incorporated into one or more other embodiments and vice versa.

The invention claimed is:

1. A multifunctional spacer kit for knee surgery comprising:
   one or more height adjusters; and
   first and second multifunctional spacers, each spacer comprising:
     a main body configured for use with a single femoral condyle and having an anterior portion of a first height and a posterior portion of a second height, wherein the second height is greater than, equal to or less than the first height,
   wherein the anterior portion and the posterior portion are each provided with an attachment mechanism for selective attachment of said one or more height adjusters,
   wherein the posterior portion of the first spacer is configured for insertion between a trial tibial component and a medial femoral condyle and the posterior portion of the second spacer is configured for insertion between a trial tibial component and a lateral femoral condyle, and when the knee is in extension one or more height adjusters may be provided on the posterior portions of the first and second multifunctional spacers in order to obtain a desired amount of collateral ligament tension on both medial and lateral sides of the knee prior to a distal femoral resection,
   wherein, in use, the posterior portion of the first spacer and any height adjuster attached to the posterior portion of the first spacer, optionally has the same thickness as the posterior portion of the second spacer and any height adjuster attached to the posterior portion of the second spacer, and
   wherein, in use, the anterior portion of the first spacer and any height adjuster attached to the anterior portion of the first spacer is configured to have the same thickness as the anterior portion of the second spacer and any height adjuster attached to the anterior portion of the second spacer, to support a cutting block.

2. The multifunctional spacer kit according to claim 1 wherein the posterior portion has a thickness of 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm or 20 mm.

3. The multifunctional spacer kit according to claim 1 wherein the anterior portion has a thickness of 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm or 20 mm.

4. The multifunctional spacer kit according to claim 1 wherein the one or more height adjusters each has a thickness of 1 mm, 2 mm, 2.5 mm, 5 mm, 7.5 mm or 10 mm.

5. The multifunctional spacer kit according to claim 1 wherein each attachment mechanism comprises one or more sockets on the spacer, and each height adjuster comprises one or more complementary plugs.

6. The multifunctional spacer kit according to claim 1 wherein the one or more height adjusters comprise a posterior height adjuster and an anterior height adjuster that are different in shape or thickness.

7. The multifunctional spacer kit according to claim 6 wherein the posterior height adjuster has a bearing surface that is substantially rectangular, substantially circular, substantially L-shaped, substantially U-shaped, substantially V-shaped or substantially O-shaped.

8. The multifunctional spacer kit according to claim 6 wherein the attachment mechanism on the posterior portion and the attachment mechanism on the anterior portion are different so as to only permit attachment of the posterior height adjuster or the anterior height adjuster, respectively.

9. The multifunctional spacer kit according to claim 1 wherein each spacer is formed from plastic, metal or ceramic.

10. The multifunctional spacer kit according to claim 1 wherein each said height adjuster is formed from plastic, metal or ceramic.

11. The multifunctional spacer kit according to claim 1, wherein the posterior portion of the first spacer is configured for insertion between the trial tibial component and the medial femoral condyle and the posterior portion of the second spacer is configured for insertion between the trial tibial component and the lateral femoral condyle, when the knee is in flexion, to obtain a desired amount of collateral ligament tension on both medial and lateral sides of the knee prior to further femoral resection.

12. The multifunctional spacer kit according to claim 1, comprising multiple first spacers and multiple second spacers, wherein the posterior portion of each multifunctional spacer has a different thickness.

* * * * *